United States Patent [19]

Morawetz et al.

[11] Patent Number: 4,922,908
[45] Date of Patent: May 8, 1990

[54] MEDICAL STIMULATOR WITH STIMULATION SIGNAL CHARACTERISTICS MODULATED AS A FUNCTION OF STIMULATION SIGNAL FREQUENCY

[75] Inventors: Peter L. Morawetz, Minneapolis; Zosim Ioffe, St. Paul, both of Minn.

[73] Assignee: Empi, Inc., St. Paul, Minn.

[21] Appl. No.: 308,999

[22] Filed: Feb. 8, 1989

Related U.S. Application Data

[63] Continuation of Ser. No. 757,705, Jul. 22, 1985, abandoned.

[51] Int. Cl.$^5$ .............................................. A61N 1/36
[52] U.S. Cl. ................................................... 128/422
[58] Field of Search ........... 128/419 E, 419 F, 419 G, 128/419 R, 421–423

[56] References Cited

U.S. PATENT DOCUMENTS

| | | | |
|---|---|---|---|
| 2,532,788 | 12/1950 | Sarnoff | 128/419 G |
| 3,096,768 | 7/1963 | Griffith, Jr. | 128/420 A |
| 3,773,051 | 11/1973 | Holcomb et al. | 128/419 G |
| 3,794,022 | 2/1974 | Nawracaj et al. | 128/420 A |
| 3,898,991 | 8/1975 | Ikuno et al. | 128/422 |
| 3,902,502 | 9/1975 | Liss et al. | 128/422 |
| 4,071,033 | 1/1978 | Nawracaj et al. | 128/420 A |
| 4,102,348 | 7/1978 | Hihara et al. | 128/422 |
| 4,148,321 | 4/1979 | Wyss et al. | 128/420 A |
| 4,153,061 | 5/1979 | Nemec | 128/420 A |
| 4,210,151 | 7/1980 | Keller, Jr. | 128/421 |
| 4,211,230 | 7/1980 | Woltosz | 128/421 |
| 4,338,945 | 7/1982 | Kosugi et al. | 128/421 |
| 4,340,063 | 7/1982 | Maurer | 128/421 |
| 4,431,002 | 2/1984 | Maurer et al. | 128/422 |
| 4,442,839 | 4/1984 | Maurer et al. | 128/419 R |
| 4,453,548 | 6/1984 | Maurer et al. | 128/421 |
| 4,528,984 | 7/1985 | Morawetz et al. | 128/421 |
| 4,530,360 | 7/1985 | Duarte | 128/419 R |
| 4,550,733 | 11/1985 | Liss et al. | 128/421 |

*Primary Examiner*—William E. Kamm
*Attorney, Agent, or Firm*—Kinney & Lange

[57] ABSTRACT

A transcutaneous electrical nerve stimulation (TENS) apparatus includes first, second, and third oscillators. The first oscillator produces a first train of pulses at a main frequency. The second oscillator produces a second train of pulses at a modulation frequency. Output levels of the second train of pulses vary as a function of the modulation frequency. A frequency control simultaneously controls both the main and modulation frequencies. The third oscillator is responsive to the first and second oscillators and produces a third train of pulses at the main frequency. Intensity and frequency of the pulses of the third pulse train are modulated as a function of the output levels of the second train of pulses. An output driver responsive to the third oscillator converts the third train of pulses into a train of stimulation pulses having electrical characteristics adapted to be applied to a human body to suppress pain.

39 Claims, 7 Drawing Sheets

Fig.6 CONTINUOUS
Fig.7 CYCLED BURST
Fig.8 MODULATED AMPLITUDE
Fig.9 MODULATED PULSE RATE
Fig.10 MULTI-MODULATED

MEDICAL STIMULATOR WITH STIMULATION SIGNAL CHARACTERISTICS MODULATED AS A FUNCTION OF STIMULATION SIGNAL FREQUENCY

This is a continuation of application Ser. No. 757,705, filed July 22, 1985 (now abandoned).

BACKGROUND OF THE INVENTION

1. Field of the Invention.

The present invention relates to medical electrical stimulation devices. In particular, the present invention is a transcutaneous electrical nerve stimulation (TENS) apparatus.

2. Description of the Prior Art.

Chronic pain is one of the most common medical problems encountered by clinicians. It is well known that through the application of electrical pulses to nerves, such as transcutaneous electrical nerve stimulation (TENS), pain can be suppressed. TENS therapy is, in fact, a proven alternative to drug therapy. Investigators have found that 55% to 60% of the chronic pain patients studied obtained satisfactory relief with TENS.

Disadvantages associated with early TENS devices are described in the Background of the Invention section of U.S. Pat. No. 4,431,002. In general, patients were unable to tolerate the unpleasant sensations which accompanied the high intensity stimulation levels necessary to produce long term analgesia. The medical stimulation apparatus disclosed in the U.S. Pat No. 4,431,002 overcomes these problems to some extent by modulating the intensity and frequency of the stimulation signal. Intensity of the stimulation signal changes as frequency of the stimulation signal varies between two levels. The result is that an increase in stimulation signal intensity due to an increase in frequency is counteracted by a simultaneous decrease in the signal intensity.

The TENS apparatus disclosed in the U.S. Pat. No. 4,431,002 modulates the intensity and frequency of the stimulation signal within preset limits, however. This technique presents several problems. The patient's perception of the stimulation signal will vary with its intensity and frequency. When the stimulation signal frequency and intensity are modulated only between predetermined intensity and frequency limits, the limits must be set at a value which can accommodate the entire range of intensity and frequency settings available. The preset limit is merely a compromise limit, however, and is optimum for only limited intensity and frequency settings. By way of example, when a stimulation signal is being produced at a low frequency of 2Hz, a 25% modulated change in its intensity would be imperceptible and useless. The same 25% modulated intensity change when the signal has a high frequency of 150Hz can, however, be intolerable to the patient.

Other problems with prior art TENS devices include the phenomena of accommodation and adaptation. Accommodation is fatigue of stimulus receptors, such as nerves. When a receptor is repeatedly subject to a given stimulus, it becomes accommodated to the stimulus, and its output level decreases. Adaptation is a similar property which occurs within the central nervous system. When the central nervous system is repeatedly subject to the same stimulus from receptors, it begins to ignore the stimulus.

It is clear that there is a continuing need for TENS devices which alleviate the problems associated with perception, accommodation, and adaptation. A TENS device which modulates characteristics of the stimulation signal as a function of a variable parameter, as opposed to within preselected limits, would be especially desirable. The degree to which characteristics are modulated should be adapted to meet the physiology of the human body. Circuitry for implementing these functions should also be relatively inexpensive to make the TENS device cost effective.

SUMMARY OF THE INVENTION

The present invention is a medical electrical stimulation apparatus which is bsed on the recognition that characteristics of the stimulation signal, including intensity, main frequency, and modulation frequency, can produce pain relief more effectively if modulated, or controlled, as a function of the main frequency. Included are means for producing a train of electrical pulses at a main frequency, and means for modulating at least one characteristic of pulses in the train as a function of the main frequency of the pulse train. Problems associated with patient perception, accommodation, and adaptation are greatly reduced. The stimulation apparatus can be comfortably and effectively used on even sensitive areas of the body.

In one preferred embodiment, the means for modulating modulates intensity of the pulses as a function of the main frequency of the pulse train. In another preferred embodiment, the means for modulating modulates frequency of the pulses as a function of the main frequency of the pulse train. In yet another preferred embodiment, the means for modulating modulates intensity and frequency of the pulses in the train as a function of main frequency.

The means for modulating intensity preferably causes intensity of the pulses of the train to switch between a first intensity level and a lower second intensity level at a modulation frequency. A difference in intensity between the first and second intensity levels is determined as a function of the main frequency. The means for modulating frequency preferably causes the frequency of the pulses of the train to switch between the main frequency and a lower second frequency at the modulation frequency. A difference in frequency between the main and second frequencies is determined as a function of the main frequency.

In other embodiments, the modulation frequency is controlled as a function of the main frequency of the pulse train. Intensity control means are used to adjust the first intensity level. Frequency control means are used to adjust the main frequency.

DETAILED DESCRIPTION OF THE PREFERRED EMBODIMENTS

The present invention is a transcutaneous electrical nerve stimulation (TENS) apparatus in which various characteristics of output stimulation signals are modulated as a function of a main frequency of the stimulation signal. Modulated characteristics include intensity and/or frequency of the stimulation signals. Intensity of the stimulation signals can be modulated by controlling amplitude and/or width of individual pulses of the stimulation signal. A modulation frequency, (i.e. the frequency at which intensity and/or frequency of the stimulation signal is varied), is also controlled as a function of the main frequency of the stimulation signal. Problems associated with prior art TENS apparatus, including perception, accommodation, and adaptation, are greatly reduced.

Figure 1:
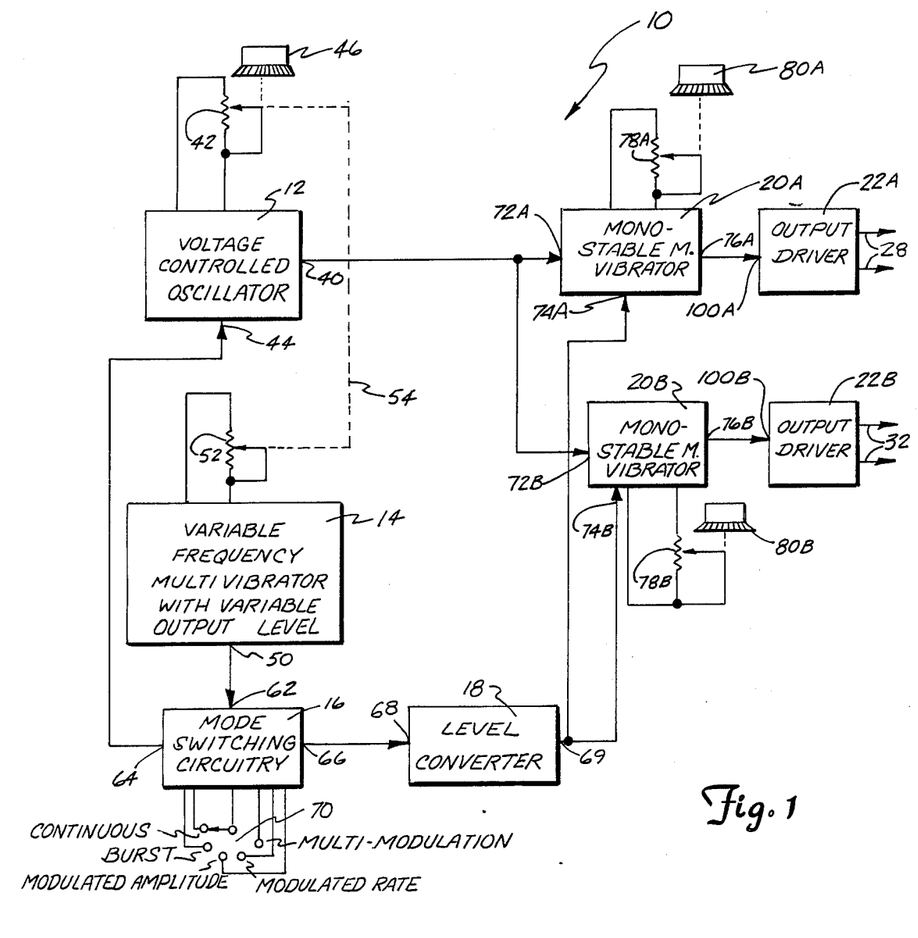
FIG. 1 is a block diagram representation of the TENS apparatus of the present invention.

A preferred embodiment of the present invention, dual-channel TENS apparatus 10, is illustrated in block diagram form by FIG. 1. As shown, TENS apparatus 10 includes voltage controlled oscillator (VCO) 12, variable frequency multivibrator with variable output levels 14, mode switching circuitry 16, level converter 18, first and second channel monostable multivibrators 20A and 20B, respectively, and first and second channel output drivers 22A and 22B, respectively. A first channel stimulation signal in the form of a first train of stimulation pulses is outputted from TENS apparatus 10 through first channel output terminals 28. The first channel stimulation signal can then be applied to the body of a patient through electrodes (not shown). Similarly, a second channel stimulation signal in the form of a second train of stimulation pulses is outputted through output terminals 32.

Voltage controlled oscillator (VCO) 12 acts as a first oscillator of TENS apparatus 10 for producing a first train of pulses having a main frequency at output terminal 40. The main frequency of the first pulse train is adjusted by frequency control 42, shown in the form of a potentiometer, through frequency control knob 46. In preferred embodiments, the main frequency of the first train of pulses can be set to any frequency between 2 and 152Hz by frequency control 42. VCO 12 can also modulate the main frequency of the first pulse train as a function of a modulation signal received on modulation input terminal 44. This feature is discussed in detail in subsequent portions of this specification.

Variable frequency multivibrator with variable output level 14 acts as a second oscillator and includes output terminal 50 and frequency control 52. Variable frequency multivibrator 14 produces a second train of pulses having a modulation frequency at output terminal 50. Modulation frequency control 52, shown in the form of a potentiometer, controls the modulation frequency at which variable frequency multivibrator 14 produces the second pulse train. In the present invention, the modulation frequency of the second pulse train is controlled as a function of the main frequency of the first pulse train. A preferred apparatus for implementing this functional relationship is a mechanical link between modulation frequency control 52 and main frequency control 42, as illustrated by dashed line 54. Adjustment of main frequency control 42 through control knob 46 therefore controls both the main and modulation frequencies. In a preferred embodiment, the modulation frequency of the second pulse train varies from 0.25Hz to 4Hz as the main frequency of the first pulse train varies from 2Hz to 152Hz. Other apparatus and methods for controlling the modulation frequency as a function of the main frequency, including electrical control, can also be used.

Figure 2:
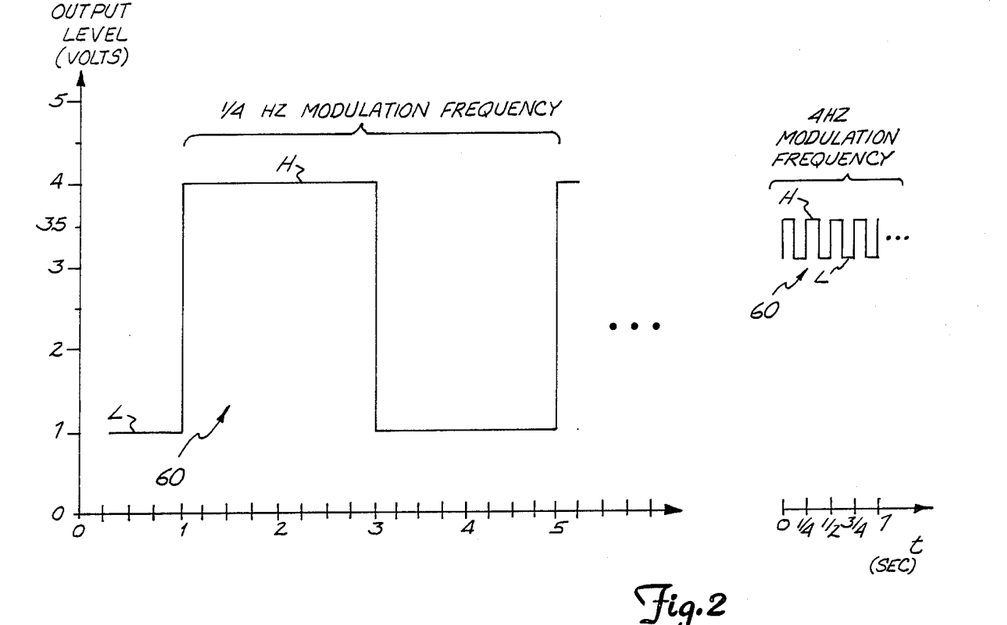
FIG. 2 is a graphic representation of how the output levels of the second pulse train produced by the variable frequency multivibrator in FIG. 1 vary with modulation frequency.

FIG. 2 illustrates the second train of pulses 60 as produced by variable frequency multivibrator 14 at output terminal 50. The output levels of second pulse train 60 vary with the modulation frequency at which the pulses are produced. In the embodiment shown, second pulse train 60 switches between a low output level, L, of 1v and a high output level, H, of 4v when the modulation frequency is equal to ¼Hz. When the modulation frequency is equal to 4Hz, variable frequency multivibrator 14 causes second pulse train 60 to switch between a low output level, L, of 3.2v and a high output level, H, of 3.5v. The particular output levels are shown in FIG. 2 simply for purposes of illustration. Other output levels at the two particular modulation frequencies can be produced by different circuit configurations of variable frequency multivibrator 14. In addition, any desired functional relationship between the output levels and the modulation frequency of second pulse train 60 can be implemented by variable frequency multivibrator 14. This functional relationship can be either linear or nonlinear.

Referring back to FIG. 1, mode switching circuitry 16 includes input terminal 62, frequency modulation output terminal 64, amplitude modulation output terminal 66, and mode select switch 70. Input terminal 62 is connected to receive the second pulse train from output terminal 50 of variable frequency multivibrator 14. Frequency modulation output terminal 64 is connected to modulation input terminal 44 of VCO 12. Amplitude modulation output terminal 66 is connected to an input terminal 68 of level converter 18.

Mode select switch 70 is operated to select a mode of operation from a set including a CONTINOUS mode, a CYCLED BURST mode, a MODULATED AMPLITUDE mode, a MODULATED PULSE RATE mode, and a MULTI-MODULATED mode. When the CONTINUOUS mode is selected by switch 70, mode switching circuitry 16 disconnects input 62 from both frequency and amplitude outputs 64 and 66, respectively.

When the CYCLED BURST mode is selected by switch 70, mode switching circuitry 16 causes input terminal 62 to be electrically connected to amplitude modulation output terminal 66, and disconnected from frequency modulation output terminal 64. Similarly, when the MODULATED AMPLITUDE mode is selected by switch 70, mode switching circuitry 16 causes input terminal 62 to be electrically connected to amplitude modulation output terminal 66 while at the same time disconnected from frequency modulation output terminal 64.

When the MODULATED PULSE RATE mode is selected by switch 70, mode switching circuitry 16 electrically connects input terminal 62 to frequency modulation output terminal 64, while disconnecting amplitude modulation output terminal 66. When the MULTI-MODULATED mode of operation is selected, both amplitude modulation output terminal 66 and frequency modulation output terminal 64 are electrically connected to input terminal 62.

Level converter 18 is connected to receive the second pulse train propogated to its input terminal 68 through mode switching circuitry 16 when the CYCLED BURST, MODULATED AMPLITUDE, or MULTI-MODULATION mode is selected. Output levels of the second pulse train are shifted by level converter 18 to levels representative of desired intensity levels of the pulses of the first and second channel stimulation signals. The particular levels to which level converter 18 shifts the second pulse train output levels is dependent upon the switching characteristics, and therefore specific circuit characteristics, of first and second monostable multivibrators 20A and 20B. In preferred embodiments, level converter 18 shifts the DC voltage level of second pulse trains 60 (shown in FIG. 2).

First and second channel monostable multivibrators 20A and 20B are identical in design and operation. The following description therefore refers to both. Components of first channel multivibrator are identified by an "A", while corresponding components on the second channel multivibrator 20B are identified by a "B."

As shown in FIG. 1, monostable multivibrator 20A includes trigger input terminal 72A, level control input terminal 74A, and output terminal 76A. Monostable multivibrator 20A acts as a third oscillator and produces a third train of pulses at its output terminal 76A as a function of the inputs received on input terminals 72A and 74A. Monostable multivibrator 20A also includes peak intensity control 78A, shown in the form of a potentiometer. Peak intensity of individual pulses of the third pulse train is controlled by intensity control 78A by adjusting peak intensity control knob 80A.

Trigger input terminal 72A is connected to output terminal 40 of VCO 12 and receives the first train of pulses at the main frequency. Level control input terminal 74A is connected to output terminal 69 of level converter 18 and receives the second train of pulses at the modulation frequency when the CYCLED BURST, MODULATED AMPLITUDE, or MULTI-MODULATED mode is selected.

Figure 3:
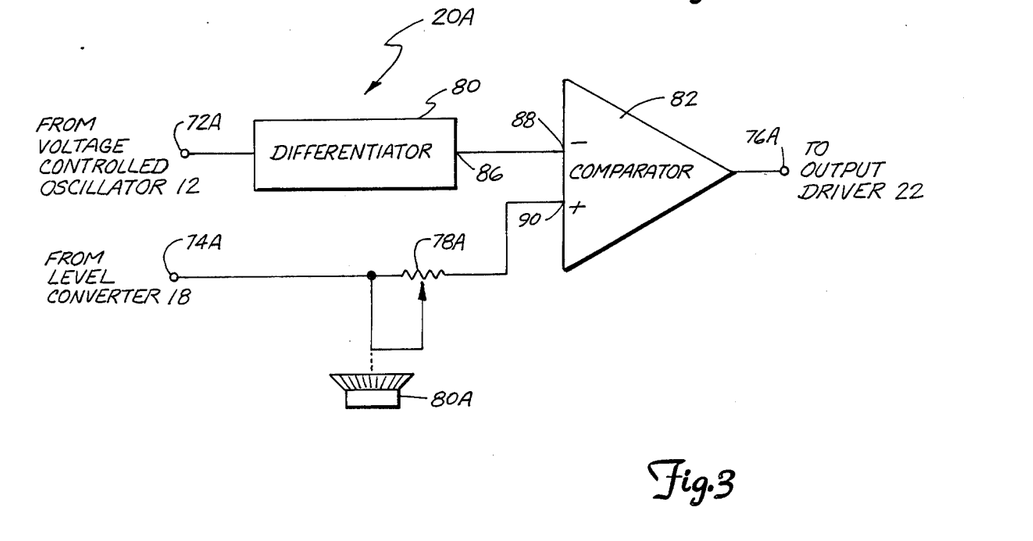
FIG. 3 is a detailed block diagram representation of the monostable multivibrator shown in FIG. 1.

Individual pulses of the third pulse train are produced by multivibrator 20A at the main frequency. Intensity levels are determined by the peak intensity as set by peak intensity control 78A, and the output levels of the second pulse train, as shifted by level converter 18. A preferred embodiment of monostable multivibrator 20A is illustrated in FIG. 3. As shown, multivibrator 20A includes differentiator 80 and comparator 82. The first train of pulses from voltage controlled oscillator 12 is received by differentiator 80 through trigger input terminal 72A. Differentiator 80 differentiates the first train of pulses and produces a signal representing a differentiated first train of pulses at its output 86. First or negative input terminal 88 of comparator 82 is connected to receive the differentiated first train of pulses. Second or positive input terminal 90 of comparator 82 is connected to receive the second train of pulses from level converter 18, through peak intensity control 78A. In the embodiment shown in FIG. 3, multivibrator 20A modulates intensity of the pulses of the third pulse train by modulating width of the individual pulses.

Figure 4:
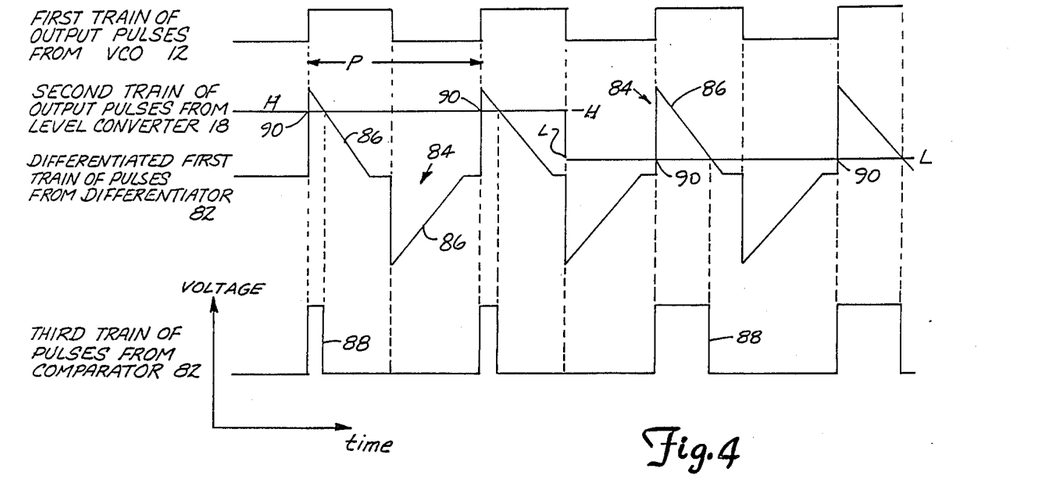
FIG. 4 is a view illustrating the operation of the monostable multivibrator shown in FIG. 1.

Operation of monostable multivibrator 20A is best described with reference to FIG. 4. The first train of pulses having the main frequency, and therefore a main period P equal to a reciprocal of the main frequency, is illustrated at the top of FIG. 4. Also shown is the differentiated first train of pulses from differentiator 82. At each pulse transition of the first pulse train differentiator 80 produces a signal intensity spike, such as voltage spikes 84. Each spike 84 has a decay ramp 86 formed when the voltage of spikes 84 decay at a decay rate determined by parameters of differentiator 80. The decay rate of each spike 84 is identical, and decay ramps 86 are therefore used as a time base to control width of pulses in the third pulse train.

As illustrated in FIG. 4, high level H, and low level L of the second pulse train are shifted to levels, preferably voltages, which are within the voltage range of differentiated pulse spikes 84. Comparator 82 initiates the production of individual pulses 88 of the third pulse train, or switches "ON," when the rising edge of spikes 84 reaches a voltage equal to that of the second pulse train, as shown at 90. Individual pulses 88 then remain "ON" for the time period during which the voltage of spikes 84 is greater than the voltage of the second pulse train. When decay ramp 86 falls to the voltage of the second pulse train, comparator 82 ends the individual pulse, and switches "OFF." Since the voltage of decay ramps 86 falls steadily over time, the width of individual pulses 88 of the third pulse train is determined directly by the relative voltage level of the second pulse train as compared to the voltage levels of differentiated spikes 84. The intensity, or width, of pulses 88 therefore varies as a function of the modulation frequency since the voltage levels of the second pulse train vary as a function of the modulation frequency.

Figure 5:
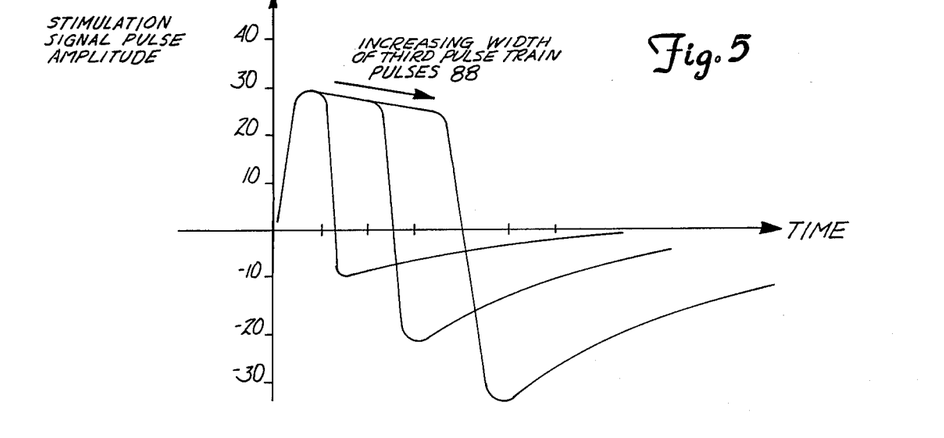
FIG. 5 is a view illustrating stimulation signal pulses produced by the output drivers shown in FIG. 1.
Figure 14:
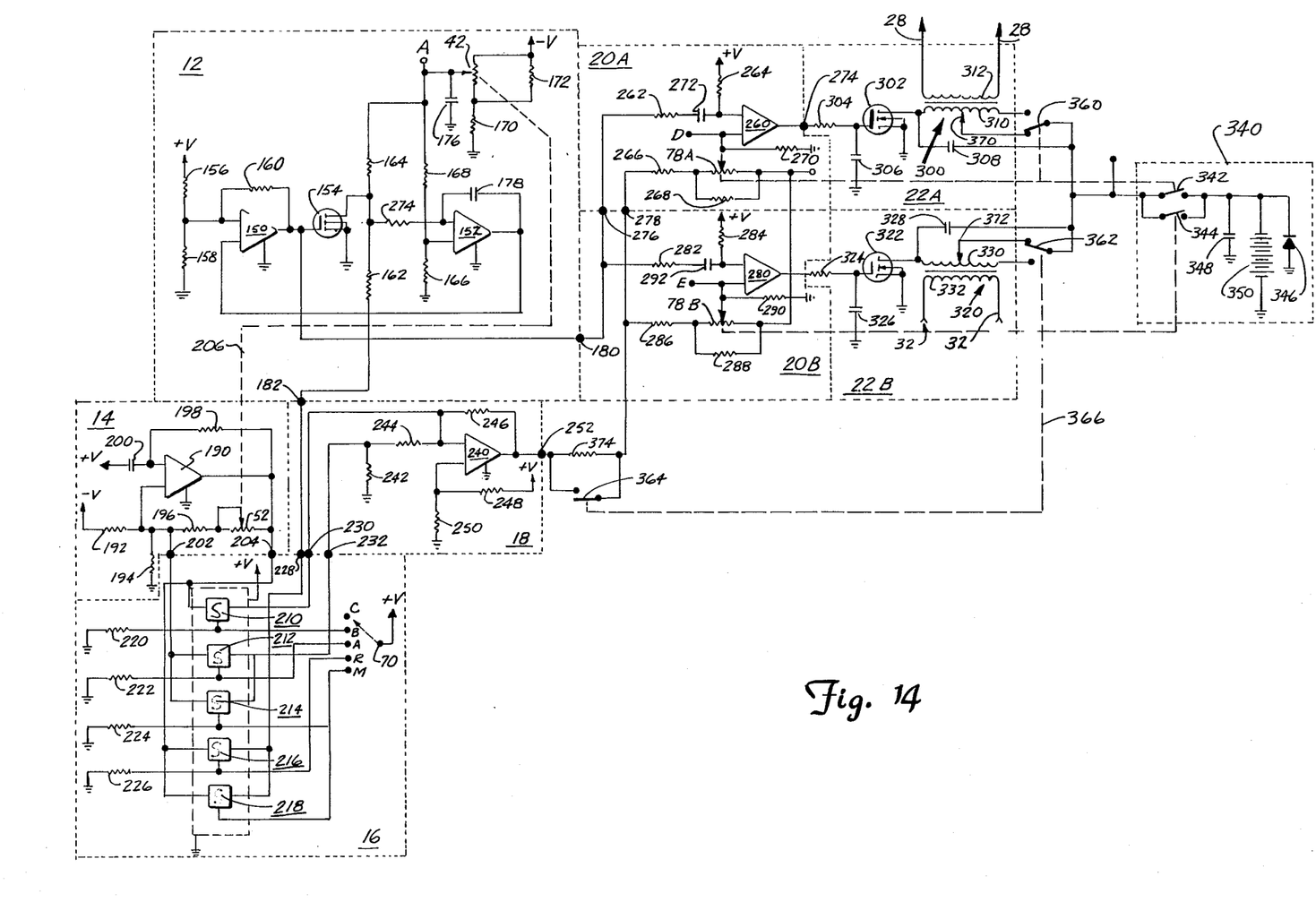
FIG. 14 is a detailed schematic diagram of the preferred embodiment of the present invention.

Referring back to FIG. 1, first and second output drivers 22A and 22B are identical in construction and operation. Each has an input 100 connected to receive the intensity modulated third train of pulses from output terminal 76 of monostable multivibrator 20. Output drivers 22A and 22B include pulse transformers 300 and 320, respectively, as shown in FIG. 14. Pulse transformers 300 and 320 convert the intensity, and in particular width, of individual pulses 88 of the third pulse train (shown in FIG. 4), to voltage and current levels adapted to be applied to a patient and thereby reduce pain. As shown in FIG. 5, output drivers 22 produce output pulses which have an intensity, including pulse width and pulse amplitude, which varies as a function of the width of the pulses 88 of the third pulse train.

Figure 6:
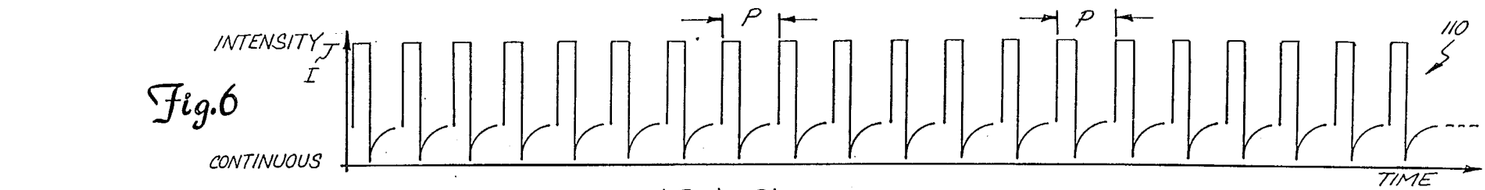
FIG. 6 illustrates the stimulation signal produced by the present invention when it is operating in its CONTINUOUS modulation mode.

The various modes of operation of TENS apparatus 10 are illustrated with reference to FIGS. 6–10. Although described below with reference to the first stimulation channel, the description is equally applicable to the second stimulation channel. The CONTINUOUS mode of operation is illustrated in FIG. 6. As previously noted, when this mode of operation is selected, mode switching circuitry 16 disconnects both frequency modulation and amplitude modulation output terminals 64 and 66, respectively, from input terminal 62. Monostable multivibrator 20A is therefore responsive only to VCO 12 and produces stimulation signal 110 with individual pulses having the main frequency, and main period P, set by main frequency control 42, and an intensity, I, set by peak intensity control 78A.

Figure 7:
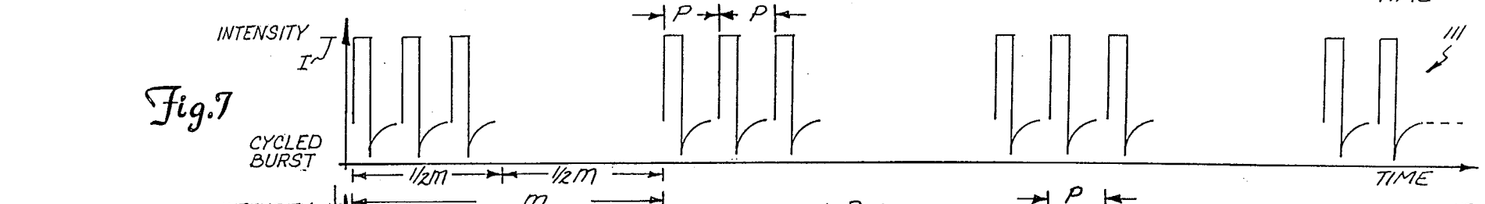
FIG. 7 illustrates the stimulation signal of the present invention when it is operating in its CYCLED BURST modulation mode.

Stimulation signal 111, produced when the CYCLED BURST mode is selected, is shown in FIG. 7. During this mode, the second pulse train is propogated through mode switching circuitry 16 and level converter 18 to amplitude control input 74A of multivibrator 20A. Level converter 18 and peak intensity control 78 causes the high level H of the second pulse train to be within the voltage range of positive going differentiated spikes 84 as shown in FIG. 4. Low level L of the second pulse train is maintained below spikes 84. Individual pulses of the stimulation signal 111 are therefore produced at the main frequency, and main period P, as set by main frequency control 42. Intensity of the individual pulses switches between an intensity level, I, set by peak intensity control 78, and a zero intensity level, at the modulation frequency of the second pulse train.

The burst frequency of stimulation signal 111 in the CYCLED BURST mode is equal to the modulation frequency of the second pulse train. Individual pulses are produced at intensity I for ½ of the modulation period M, and at the zero intensity level for the following ½ modulation period M. Since the modulation frequency is controlled simultaneously with the main frequency, the burst frequency is set as a function of the main frequency.

Figure 8:
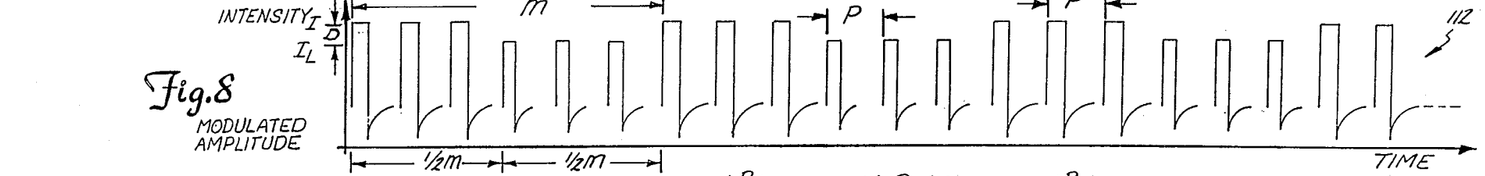
FIG. 8 illustrates the stimulation signal of the present invention when it is operating in its MODULATED AMPLITUDE modulation mode.

Stimulation signal 112, produced when the MODULATED AMPLITUDE mode is selected, is illustrated in FIG. 8. During this mode, like the CYCLED BURST mode, the second pulse train is propogated through mode switching circuitry 16 and level converter 18 to level control input 74A of multivibrator 20A. In this mode, however, level converter 18 causes both high level H and low level L of the second pulse train to be within the voltage range of positive-going differentiated spikes 84. Individual pulses of MODULATED AMPLITUDE stimulation signal 112 are therefore produced at the main frequency and main period P set by main frequency control 42. Intensity of the pulses varies between a first intensity I, as set by peak intensity control 78A, and a second lower intensity $I_L$, at the modulation frequency and modulation period M of the second pulse train. Since the modulation frequency is controlled simultaneously with the main frequency, the frequency at which MODULATED AMPLITUDE stimulation signal 112 switches between peak intensity I and lower intensity $I_L$ is set as a function of the main frequency.

The difference in intensity, D, between peak intensity I and the second lower intensity $I_L$, (i.e. the "depth of modulation"), is determined as a function of the difference between the high and low voltage levels, H and L, respectively, of the second pulse train. Since the high and low voltage levels are controlled as a function of the modulation frequency of variable frequency multivibrator 14, and the modulation frequency is in turn controlled simultaneously with the main frequency, the depth of modulation of MODULATED AMPLITUDE stimulation signal 112 is determined as a function of the main frequency.

Figure 12:
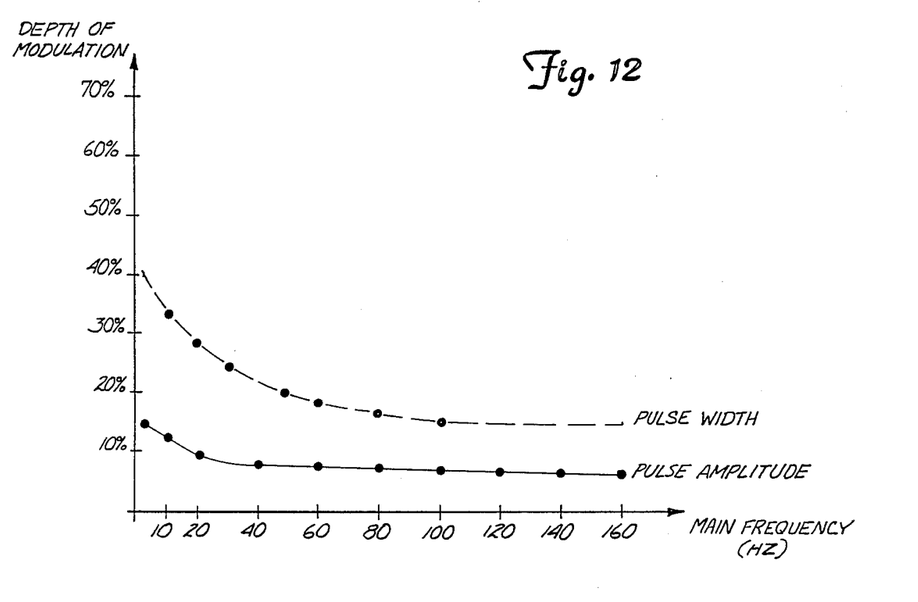
FIG. 12 is a graphic representation of pulse width and pulse amplitude depth of modulation as a function of main frequency when the device is operating in its NARROW-TRACK pulse-tracking mode.

One preferred relationship between main frequency and depth of modulation, that being for a first or wide-track stimulation pulse waveform described in detail in a later portion of this description, is illustrated in FIG. 12. As shown in FIG. 12, pulse width depth of modulation decreases nonlinearly from 40% at a 2Hz main frequency, to approximately 15% at 152Hz. Pulse amplitude depth of modulation decreases nonlinearly from a high of 15% at 2Hz down to approximately 9% at 152Hz.

Figure 11:
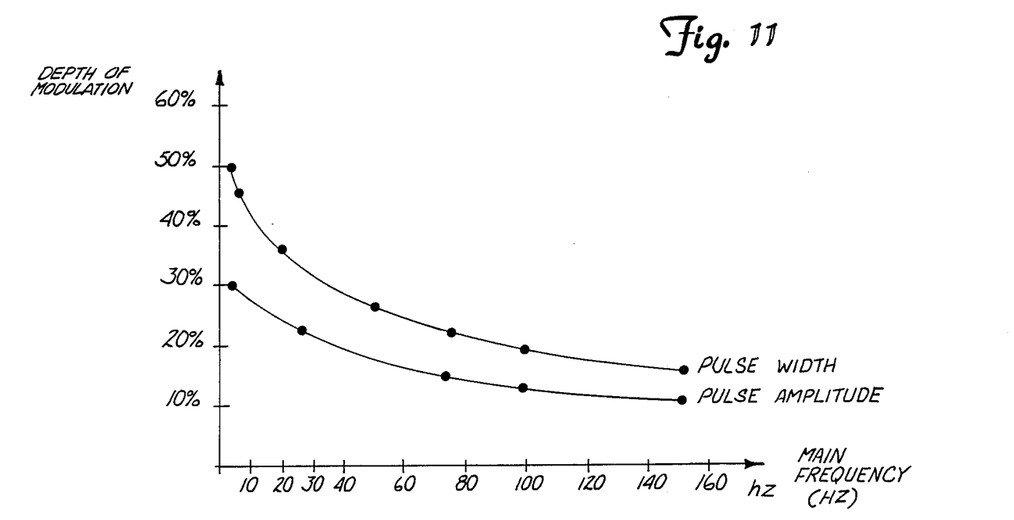
FIG. 11 is a graphic representation of the depth of modulation of pulse width and pulse amplitude as a function of main frequency when the present invention is operating in its WIDE-TRACK pulse-tracking pulse mode.

A second preferred relationship between main frequency and depth of modulation, that for a second or narrow-track stimulation pulse waveform is illustrated in FIG. 11. As shown, a depth of pulse width modulation decreases nonlinearly from a high of 50% at 2Hz to a low of approximately 15% at 152Hz. Depth of pulse amplitude modulation decreases nonlinearly from a high of 30% at 2Hz to a low of approximately 11% at 152Hz. Other functional relationships between main frequency and pulse intensity modulation can also be implemented by varying circuit parameters.

Figure 9:
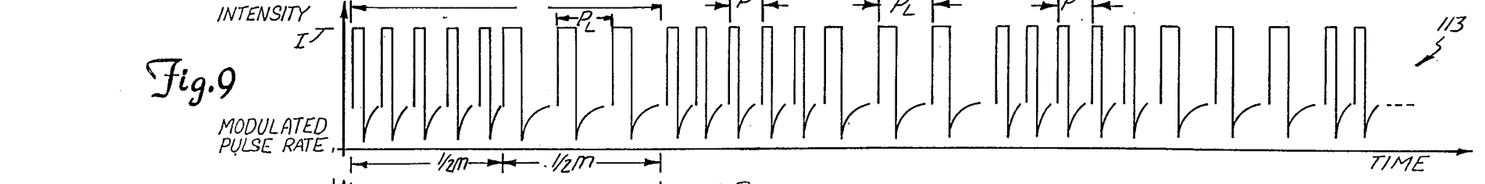
FIG. 9 illustrates the stimulation signal produced by the present invention when it is operating in its MODULATED PULSE RATE modulation mode.

Stimulation signal 113, produced when the MODULATED PULSE RATE mode is selected, is illustrated in FIG. 9. During this mode, the second pulse train is propogated through mode switching circuitry 16 to modulation input terminal 44 of VCO 12. Individual pulses of stimulation signal 113 are produced at an intensity I set by peak intensity control 78A. Since VCO 12 is being modulated by the second pulse train, frequency at which the individual pulses of stimulation signal 113 are produced is also modulated. As shown in FIG. 9, individual pulse frequency switches between a first frequency, the main frequency and main period P as set by main frequency control 42, and a second lower frequency having a second period $P_L$. Since the modulation frequency of the second pulse train is controlled simultaneously with the main frequency, the modulation frequency, as represented by modulation period M in FIG. 9, at which stimulation signal 113 switches between the main frequency and the lower frequency is determined as a function of the main frequency.

The difference in frequency between the main frequency and the lower frequency at which stimulation signal 113 is produced is determined as a function of the high and low voltage levels H and L, respectively, of the second train of pulses. Since these levels vary as a function of modulation frequency, and modulation frequency is controlled as a function of the main frequency, the difference in frequency between the main frequency and lower frequency is determined as a function of the main frequency.

Figure 13:
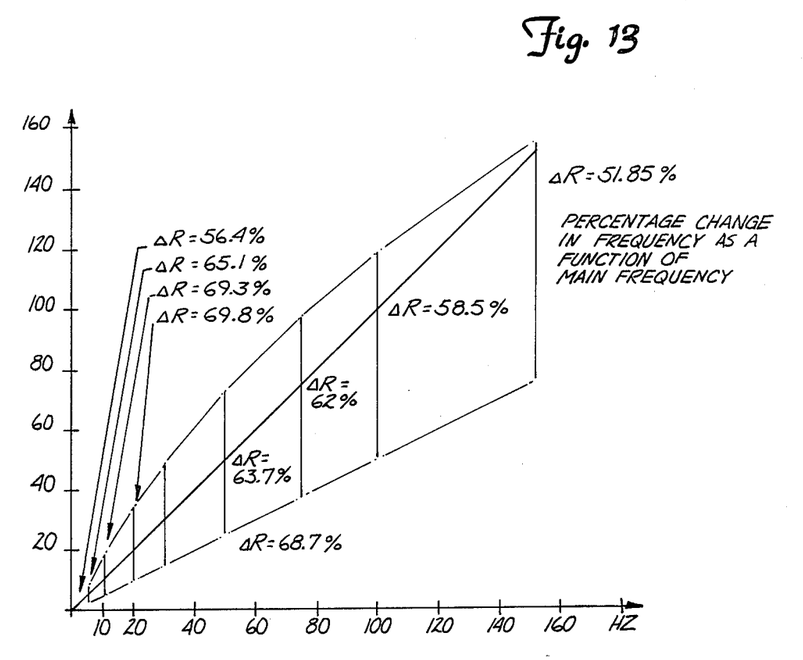
FIG. 13 is a graphic representation of the percentage change in frequency as a function of main frequency when the present invention is operating in its MODULATED PULSE RATE and MULTI-MODULATED modulation modes.

A preferred embodiment of the relationship between main frequency and the difference in frequency in the MODULATED PULSE RATE mode is illustrated in FIG. 13. As shown, the percentage of frequency difference varies from 56.4% at a main frequency of 2Hz up to a difference of 69.8% at 20Hz. The percentage difference in frequency then decreases to 51.9% as main frequency further increases to 152Hz. Other relationships, whether they be linear or nonlinear, between percentage change in frequency as a function of main frequency can also be used.

Figure 10:
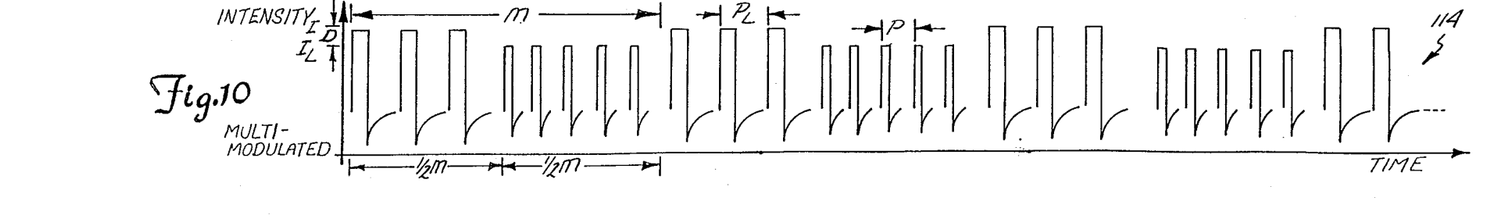
FIG. 10 illustrates the stimulation signal of the present invention when it is operating in its MULTI-MODULATED modulation mode.

Stimulation signal 114, produced when the MULTI-MODULATED mode is selected, is illustrated in FIG. 10. During this mode, the second pulse train is propogated through mode switching circuitry 16 and level converter 18 to level control input 74A of multivibrator 20A. The second pulse train is also propogated through mode switching circuitry 16 to modulation input 44 of VCO 12. Both intensity and frequency of individual pulses of stimulation signal 114 are thereby modulated as a function of the main frequency. The MULTI-MODULATED mode of operation is in effect a combination of the MODULATED AMPLITUDE mode, and the MODULATED PULSE RATE mode.

During one-half of modulation period M, individual pulses of stimulation signal 114 are produced by multivibrator 20A at intensity I set by peak intensity control 78A, and at the second lower frequency having a period $P_L$. During the second half of modulation period M, multivibrator 20A produces pulses of stimulation signal 114 at the second lower intensity level $I_L$, and with the main frequency as represented by main period P. As previously described, the modulation frequency, the depth of intensity modulation, D, and the difference between modulated frequencies, are all determined as a function of the main frequency. The functional relationships between main frequency and these characteristics can be the same as those illustrated in FIGS. 11, 12 and 13.

FIG. 14 is a detailed schematic representation of TENS apparatus 10. Voltage controlled oscillator 12 includes amplifiers 150 and 152, FET 154, resistors 156, 158, 160, 162, 164, 166, 168, 170, 172, and 174, and capacitors 176 and 178. Output terminal 40 of VCO 12, as shown in FIG. 2, is represented by node 180. Modulation input terminal 44 is represented by node 182. The main frequency at which VCO 12 produces the first train of pulses is controlled by potentiometer 42.

Variable frequency multivibrator with variable output level 14 is comprised of amplifier 190, resistors 192, 194, 196, and 198, and capacitor 200. Output terminal 50 of variable frequency multivibrator 14, as illustrated in FIG. 1, is represented by nodes 202 and 204 in FIG. 14. Potentiometer 52 is used to control the modulation frequency of the second pulse train. Dashed line 206 interconnecting potentiometer 52 and potentiometer 42 of VCO 12 indicates a mechanical link between these two devices.

Mode switching circuitry 16 is comprised of 5-position mechanical mode switch 70, electronic switches 210, 212, 214, 216, and 218, and resistors 220, 222, 224, and 226. Frequency modulation output terminal 64 as shown in FIG. 1, is represented in FIG. 14 by node 228. Amplitude modulation output terminal 66, as shown in FIG. 1, is represented by nodes 230 and 232 in FIG. 14.

When the CYCLED BURST mode of operation, "B", is selected by switch 70, electronic switch 210 is actuated and propogates the second pulse train from node 204 of multivibrator 14 to node 230. When the MODULATED AMPLITUDE mode of operation, "A", is selected by switch 70, electronic switch 212 is actuated and propogates the second pulse train from node 202 of multivibrator 14 to node 232. When the MODULATED PULSE RATE mode of operation, "R", is selected by switch 70, electronic switch 216 is actuated and propogates the second pulse train from node 204 of multivibrator 14 to node 228. When the MULTI-MODULATED mode of operation, "M", is selected by switch 70, electronic switches 214 and 218 are actuated. When actuated, electronic switch 214 propogates the second pulse train from node 202 of multivibrator 14 to node 232. Electronic switch 218, when actuated, propogates the second pulse train from node 204 to node 228.

Level converter 18 is comprised of amplifier 240 and resistors 242, 244, 246, 248, and 250. Output 69 of level converter 18, as shown in FIG. 1, is represented in FIG. 14 by node 252. Input terminal 68 of level converter 69, as shown in FIG. 1, is represented by nodes 230 and 232 in FIG. 14. Level converter 18 shifts the levels of the second train of pulses present on nodes 230 and 232 in a similar manner. The amount by which the high and low output levels of the second pulse train are shifted is different due to resistors 242 and 244. Node 230 is used when the CYCLED BURST mode is selected, and node 232 for the MODULATED AMPLITUDE and MULTI-MODULATED modes.

First monostable multivibrator 20A is formed by amplifier 260, resistors 262, 264, 266, 268, and 270, and capacitor 272. Resistors 262 and 264, and capacitor 272 represent differentiator 80 as shown in FIG. 3. Output 76A as shown in FIG. 1, is illustrated by node 274. Trigger input terminal 72A, as shown in FIG. 1, is represented by node 276 while level control input terminal 74A, also shown in FIG. 1, is represented by node 278. The peak width of the third pulse train pulses is controlled by peak intensity control potentiometer 78A.

Second monostable multivibrator 20B is identical to that of first monostable multivibrator 20A and includes amplifier 280, resistors 282, 284, 286, 288, and 290, as well as capacitor 292, and potentiometer 78B.

First channel output driver 22A is comprised of transformer 300, FET 302, resistor 304, and capacitors 306 and 308. Transformer 300 is a pulse-type transformer and includes primary winding 310 and secondary winding 312. The first channel stimulation signal is produced at the secondonary winding 312 through output terminals 28. Transformer 300 is preferably and air gap transformer which is critically or slightly overdamped to produce output waveforms like those illustrated in FIG. 5 when driven by width modulated pulses.

Second channel output driver 22B is identical to first channel output driver 22A and includes transformer 320, FET 322, resistor 324, and capacitors 326 and 328. Transformer 320 is formed by a primary winding 330 and secondary winding 332. A second channel stimulation signal is produced by secondary winding 332 at second channel output terminals 32.

TENS apparatus 10, as shown in FIG. 14, also includes power supply 340. Power supply 340 includes first and second channel switches 342 and 344, respectively, diode 346, and capacitor 348. Power can be provided by battery 350.

As previously mentioned, TENS apparatus 10 can be operated in several different pulse-tracking modes. In the embodiment illustrated in FIG. 14, TENS apparatus 10 includes pulse-tracking mode select switches 360, 362, and 364, each of which is mechanically linked as shown by dashed line 366. Switches 360, 362, and 364 are actuated together to select either a first or NAR- ROW-TRACK mode, or a second or WIDE-TRACK mode.

When the NARROW-TRACK mode is selected, switches 360 and 362, respectively, cause primary windings 310 and 330, respectively, to be shortened through center-taps 370 and 372, respectively. Switch 364 also causes resister 374 to be positioned in the circuit path between level converter 18 and first and second multivibrators 20A and 20B, respectively. With resister 374 in the circuit path, width of individual pulses of the second pulse trains produced by multivibrators 20A and 20B can increase from 0 to approximately 200 microseconds as their respected intensity controls are adjusted over their range.

Figure 15:
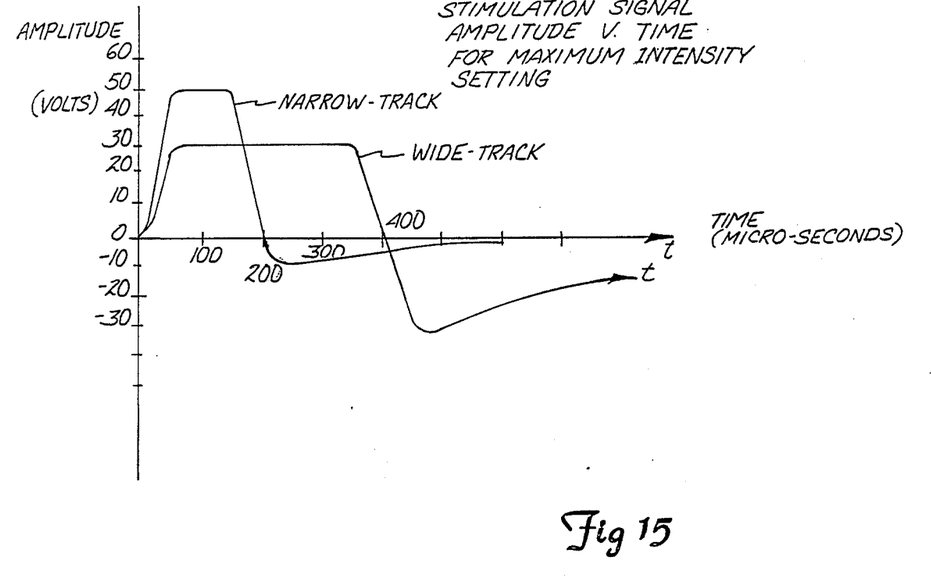
FIG. 15 is a graphic illustration of stimulation signal amplitude versus time for both a NARROW-TRACK and WIDE-TRACK pulse at maximum intensity setting.

Pulse transformers 300 and 320 have a relatively high step-up ratio of approximately 10. As a result, individual pulses of the stimulation signals are produced at a large positive amplitude, and narrow width, as illustrated in FIG. 15. Narrow-track waveforms of this type are useful for treating sensitive areas such as the cervical spine and face.

When the WIDE-TRACK pulse mode is selected, switch 364 shorts resistor 370 and causes multivibrators 20A and 20B to increase width of pulses of the third pulse train to a maximum width of approximately 400 microseconds as their respective intensity controls 78A and 78B are adjusted to the maximum setting. Switches 360 and 362 also cause the full length of primary windings 310 and 330 of transformers 300 and 320, respectively, to be interconnected in the circuit. Transformers 300 and 320 therefore have a relatively low step-up ratio, preferably about 5, when the WIDE-TRACK mode is selected.

Figure 16:
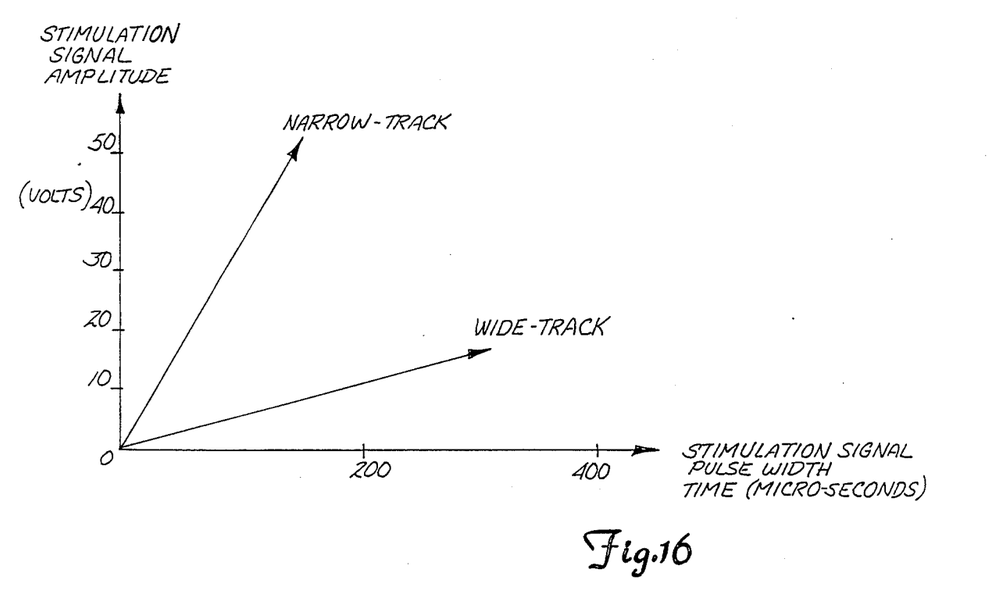
FIG. 16 is a graph of stimulation signal amplitude versus pulse width for both the NARROW-TRACK and WIDE-TRACK pulse modes of operation.

As shown in FIG. 15, the WIDE-TRACK stimulation signal pulses have a relatively greater width and lower positive amplitude than a NARROW-TRACK pulse at the same intensity setting. Since the WIDE-TRACK pulse is wider, transformers 300 and 320 cause them to have a larger undershoot or negative amplitude. One preferred pulse amplitude to pulse width relationship for the NARROW- and WIDE-TRACK pulse modes is illustrated in FIG. 16. Other relationships can of course also be used.

In conclusion, the present invention is a TENS device in which the range of intensity and frequency modulation, as well as the frequency of modulation, are varied as a function of the main frequency of the stimulation signal. The modulated waveforms produced by this TENS device are effective in treating pain. They are also well adapted for patient comfort, and alleviate the problems associated with physiological perception, and nervous system accommodation and adaptation.

Although the present invention has been described with reference to preferred embodiments, workers skilled in the art will recognize that changes may be made in form and detail without departing from the spirit and scope of the invention.

What is claimed is:

1. A medical electrical stimulation apparatus including:
   means for producing a train of electrical pulses at a main frequency;
   means for adjustably controlling the main frequency;
   means for modulating at least one characteristic of pulses in the train at a modulation frequency;
   means for controlling the modulation frequency as a function of the main frequency of the pulse train; and
   terminal means for coupling the modulated train of electrical pulses to electrodes.

2. The stimulation apparatus of claim 1 wherein the means for modulating at least one characteristic includes means for modulating intensity of the pulses in the pulse train.

3. The stimulation apparatus of claim 2 wherein the means for modulating intensity includes means for modulating amplitude of the pulses in the train.

4. The stimulation apparatus of claim 2 wherein the means for modulating intensity includes means for modulating width of the pulses in the train.

5. The stimulation apparatus of claim 2 wherein the means for modulating intensity includes means for simultaneously modulating amplitude and width of pulses in the train.

6. The stimulation apparatus of claim 2 wherein the means for modulating intensity includes means for causing intensity of the pulses of the pulse train to vary between a first intensity level and a second intensity level at the modulation frequency, and means for causing a difference in intensity between the first and second intensity levels to be determined as a function of the main frequency of the pulse train.

7. The stimulation apparatus of claim 6 wherein the means for causing intensity of the pulses in the train to vary includes means for causing intensity of the pulses to switch between the first and second intensity levels at the modulation frequency.

8. The stimulation apparatus of claim 6 wherein the means for causing intensity of the pulses of the pulse train to vary includes means for causing the difference in intensity between the first and second intensity levels to decrease as the main frequency incareases, and to increase as the main frequency decreases.

9. The stimulation apparatus of claim 6 wherein the means for causing intensity of the pulses of the pulse train to vary includes means for causing the second intensity level to be a lower intensity than the first intensity level.

10. The stimulation apparatus of claim 6 and including means for adjusting the first intensity level.

11. The stimulation apparatus of claim 1 and including means for adjusting the main frequency of the pulse train.

12. The stimulation apparatus of claim 11 wherein the means for controlling the modulation frequency includes means for causing the modulation frequency to increase as the main frequency increases, and to decrease as the main frequency decreases.

13. The stimulation apparatus of claim 11 wherein the means for controlling the modulation frequency includes means for causing the modulation frequency to increase as the main frequency increases, and to decrease as the main frequency decreases.

14. The stimulation apparatus of claim 1 wherein the means for modulating at least one characteristic includes means for modulating frequency of the pulses in the pulse train.

15. The stimulation apparatus of claim 14 and including means for adjusting intensity of the pulses in the pulse train.

16. The stimulation apparatus of claim 14 wherein the means for modulating frequency includes means for causing frequency of the pulses in the train to vary between a first frequency and a second frequency at the modulation frequency, and and means for causing a difference in frequency between the first and second frequencies to be determined as a function of the main frequency of the pulse train.

17. The stimulation apparatus of claim 16 wherein the means for modulating frequency includes means for causing the frequency of the pulses in the train to switch between the first and second frequencies at the modulation frequency.

18. The stimulation apparatus of claim 16 wherein the means for modulating frequency includes means for causing the first frequency to be the main frequency, and means for causing the second frequency to be a lower frequency than the main frequency.

19. The stimulation apparatus of claim 16 wherein the means for modulating frequency includes means for causing the difference in frequency to increase from a first difference to a second difference as main frequency increases from a first main frequency to a second main frequency, and to decrease from the second difference to a third difference as main frequency increases from the second main frequency to a third main frequency.

20. The stimulation apparatus of claim 16 and further including means for adjusting the main frequency of the pulse train.

21. The stimulation apparatus of claim 1 wherein the means for modulating at least one characteristic includes means for modulating intensity of pulses in the pulse train, and means for modulating frequency of the pulses in the pulse train.

22. The stimulation apparatus of claim 21 wherein:
the means for modulating intensity includes means for causing the intensity of the pulses of the pulse train to switch between a first intensity level and a second intensity level at a modulation frequency, and means for causing a difference in intensity between the first and second intensity levels to be determined as a function of the main frequency; and
the means for modulating frequency includes means for causing the frequency of the pulses of the pulse train to switch between a first frequency and a second frequency at the modulation frequency, and means for causing a difference in frequency between the first and second frequencies to be determined as a function of the main frequency.

23. The stimulation apparatus of claim 22 wherein:
the means for modulating intensity includes means for causing the second intensity level to be a lower intensity than the first intensity level; and
the means for modulating frequency includes means for causing the first frequency to be the main frequency, and the second frequency to be a lower frequency than the main frequency.

24. The stimulation apparatus of claim 22 wherein the means for modulating intensity includes means for causing the pulses of the train to have the first intensity level when the pulses of the train are produced at the second frequency, and for causing the pulses of the train to have the second intensity level when the pulses of the train are produced at the first frequency.

25. The stimulation apparatus of claim 22 wherein the means for modulating intensity includes means for causing the difference in intensity between the first and second intensity levels to decrease with increasing main frequency, and to increase with decreasing main frequency.

26. The stimulation apparatus of claim 22 wherein the means for modulating frequency includes means for causing the difference in frequency to increase from a first difference to a second difference as main frequency increases from a first main frequency to a second main frequency, and to decrease from the second difference to a third difference as main frequency increases from the second main frequency to a third main frequency.

27. The stimulation apparatus of claim 23 and further including:
means for adjusting the first intensity level; and
means for adjusting the main frequency.

28. The stimulation apparatus of claim 21 wherein the means for controlling the modulation frequency includes means for causing the modulation frequency to increase with increasing main frequency, and to decrease with decreasing main frequency.

29. The stimulation apparatus of claim 1 wherein the means for modulating at least one characteristic includes means for controlling intensity levels of the pulses in the pulse train as a function of the main frequency of the pulse train.

30. The stimulation apparatus of claim 1 wherein the means for modulating at least one characteristic includes means for controlling frequency of the pulses in the pulse train as a function of the main frequency of the pulse train.

31. The stimulation apparatus of claim 1 wherein the means for modulating at least one characteristic includes means for controlling intensity levels of the pulses as a function of the main frequency of the pulse train, and means for controlling frequency of the pulses as a function of the main frequency of the pulse train.

32. The stimulation apparatus of claim 1 wherein:
the apparatus further includes means for switching intensity of the pulses of the pulse train between a first intensity level and a zero intensity level at a burst frequency; and
the means for modulating at least one characteristic includes means for modulating the burst frequency of the pulse train.

33. The stimulation apparatus of claim 32 wherein the means for modulating the burst frequency includes means for causing the burst frequency to increase with increasing main frequency, and to decrease with decreasing main frequency.

34. The stimulation apparatus of claim 32 and further including means for adjusting the main frequency.

35. The stimulation apparatus of claim 32 and further including means for adjusting the first intensity level.

36. Apparatus for electrically stimulating living tissue, including:
oscillator means for producing a train of electrical pulses at a main frequency;
control means coupled to the oscillator means for controlling the main frequency;
modulation means for varying intensity of pulses of the train at a modulation frequency between a first intensity level and a second intensity level which differ in intensity as a function of the main frequency; and
electrode means for coupling the modulated train of electrical pulses to electrodes.

37. Apparatus for electrically stimulating living tissue, including:
oscillator means for producing a train of electrical pulses at a main frequency;
control means coupled to the oscillator means for controlling the main frequency;
modulating means for varying the main frequency of pulses of the train at a modulation frequency between a first frequency and a second frequency which differ in frequency as a function of the main frequency; and electrode means for coupling the modulated train of electrical pulses to electrodes.

38. Apparatus for electrically stimulating living tissue, including:

oscillator means for producing a train of electrical pulses at a main frequency;

control means coupled to the oscillator means for controlling the main frequency;

modulation means for modulating the train of electrical pulses between a first intensity level and a zero intensity level at a burst frequency which is a function of the main frequency; and electrode means for coupling the modulated train of electrical pulses to electrodes.

39. Apparatus for electrically stimulating living tissue, including:

oscillator means for producing a train of electrical pulses at a main frequency;

control means coupled to the oscillator means for controlling the main frequency intensity modulation means for varying intensity of the pulses of the train between a first intensity level and a second intensity level at a modulation frequency, and for causing a difference in intensity between the first and second intensity levels to be determined as a function of the main frequency;

frequency modulation means for modulating the main frequency of the train of electrical pulses between a first frequency and a second frequency, and for causing a difference in frequency between the first and second frequencies to be determined as a function of the main frequency; and electrode means for coupling the modulated train of electrical pulses to electrodes.

* * * * *